| United States Patent [19] | [11] Patent Number: 4,912,237 |
|---|---|
| Zeitsch | [45] Date of Patent: Mar. 27, 1990 |

[54] PROCESS FOR PRODUCING FURFURAL

[75] Inventor: Karl J. Zeitsch, Cologne, Fed. Rep. of Germany

[73] Assignee: Fried. Krupp Gesellschaft mit Beschrankter Haftung, Essen, Fed. Rep. of Germany

[21] Appl. No.: 295,314

[22] Filed: Jan. 9, 1989

[30] Foreign Application Priority Data

Jan. 8, 1988 [DE] Fed. Rep. of Germany ....... 3800317
Dec. 20, 1988 [DE] Fed. Rep. of Germany ....... 3842825

[51] Int. Cl.$^4$ ............................................. C07D 307/50
[52] U.S. Cl. ...................................................... 549/489
[58] Field of Search ............................................ 549/489

[56] References Cited

U.S. PATENT DOCUMENTS 4,401,514 8/1983 Kanzler et al. ................. 549/489 X
4,533,743 8/1985 Medeiros et al. .................... 549/489

*Primary Examiner*—Richard L. Raymond
*Attorney, Agent, or Firm*—Herbert Dubno

[57] ABSTRACT

A feed suspension of pentosan-containing organic raw materials in dilute sulfuric acid is passed with low residence time through a flow reactor heated by high-pressure steam to 170°–230° C. and then through a cooler in which it is cooled to 140°–200° C. before the suspension is admitted to a flash evaporating unit from which a furfural-rich vapor phase is separated from the residual suspension. Process water is recovered from the residual suspension and recycled for the preparation of the feed suspension. From the vapor phase, furfural is recovered by distillation, either directly or after liquefaction. In the latter case, partial condensation in a primary condenser can be used to increase the furfural concentration in the final condenser, the condensate of the primary condenser being recycled for the preparation of the feed suspension.

8 Claims, 3 Drawing Sheets

PROCESS FOR PRODUCING FURFURAL

FIELD OF THE INVENTION

My present invention relates to a process for the production of furfural from pentosan containing raw materials by hydrolysis and dehydration in an acid medium. The invention also relates to an apparatus for carrying out this process.

BACKGROUND OF THE INVENTION

Furfural is produced on an industrial scale from agricultural wastes, for example, oat hulls, bagasse, corn cob residue and saw dust and like wood residues or straw. All of these materials contain pentosan which is initially hydrolyzed to pentose with the take-up of water in accordance with the relationship:

$$(C_5H_8O_4)_n + n\ H_2O \rightarrow n\ C_5H_{10}O_5 \tag{1}$$

The pentose is then converted to furfural in a dehydration reaction in accordance with the relation:

$$C_5H_{10}O_5 - 3\ H_2O \rightarrow C_5H_4O_2 \tag{2}$$

The process can be carried out either on a batch basis or continuously.

In the batch process used generally throughout the world, utilizing the principles of the Quaker Oats process described by H. J. Brownlee and Carl S. Miner in Industrial Development of Furfural, Ind. Engng. Chem. 40 (1948) 201–204, comminuted raw material moistened with dilute sulfuric acid is treated at 153° C. and 5 ATM with steam in a reactor which rotates slowly to circulate the raw material. Steam supply and product vapor discharge are effected via the stub shafts of the reactor. The process conditions for the reactor are optimized and then maintained for industrial scale production. The residence time of a charge under these process conditions is usually about 5 hours.

The much later developed continuous process of Escher Wyss or Rosenlew utilizes the Quaker Oats principle of moistening the raw material particles with dilute sulfuric acid, but utilizes tall-shaft reactors in which the raw material is introduced from above through a gate in the reactor. The raw material descends in counterflow from the steam which is introduced from below in a fluid-bed system and the vapor is discharged. The reactor operates at a temperature of up to 184° C. and at a pressure of up to 11 ATM. The residence time in the reactor is about ½ hour.

Problems with this continuous process result from the gating of the solids into and out of the reactor, and from the fact that the steam must not only serve as a reactant but also must function as a carrier medium which reduces the efficiency because of the coupling of the chemical process with the mechanical process, etc.

Because of the fact that the particle size of the raw material is not uniform, the residence time range in the reactor for individual particles is quite wide which gives rise to a number of drawbacks effecting the chemical process.

Apart from the aforementioned processes used commercially for the production of furfural, mention can be made of a number of known processes in which furfural is recovered as a practically unavoidable by-product. This is case, for example, in the cleaning of waste waters from the woodworking industry or the manufacture of ethanol.

In a process for the production of glucose, an intermediate product in ethanol production, as described in the report "High Temperature Acid Hydrolysis of Biomass Using an Engineering-Scale Plug Flow Reactor: Results of Low Solids Testing" of Brennan, Hoaglund and Schell, (Bioltechnology and Bioengineering Symp. No. 17; 1986), industrial tests are shown to yield furfural in reduced quantities as a by-product and insofar as possible as a product which is utilized to improve the economies of the process by increasing the cash flow of the ethanol-producing apparatus.

In this process comminuted wood together with dilute sulfuric acid is heated under pressure with saturated steam in a plug-flow reactor.

In the reactor cellulose is hydrolyzed to glucose, a product which is then fermented for the production of ethanol. Water is separated by expansion into an expansion vessel in the form of steam. The steam or water vapor contains small amounts of furfural at low concentrations which appear to result as a by-product from the hydrolysis of the wood to glucose.

U.S. Pat. No. 4,533,743 describes a furfural-making process in which furfural is made from a pentose solution.

The production of the pentose solution from a pentosan-containing solid is not described in this patent. In this process, the solids-free pentose solution after traversing the reactor is cooled by heat abstraction without the formation of a vapor phase. The yield of furfural is comparatively small in this system as is the furfural concentration in the products obtained.

Both the batch process and the continuous process as well as the experimental production of ethanol with a plug flow reactor as described, operate with acid medium, usually with sulfuric acid, because the speed of the reactions of relations (1) and (2) are directly proportional to the hydrogen ion concentration. Acceleration of the reaction represented by the equation (2) is highly desirable because this reaction is the slowest step and therefore is the rate-determining step of the overall reaction. From equations (1) and (2), it is possible to ascertain that the overall reaction for the production of furfural from pentosan-containing raw material is:

$$(C_5H_8O_4)_n \rightarrow n\ C_5H_4O_2 + 2n\ H_2O \tag{3}$$

From this reaction equation it can be readily seen that the maximum possible furfural yield is 72.7% of the pentosan. In practice, however, the best that can be obtained is ⅓ of this value. Even raw materials which have relatively high pentosan contents and thus the greatest potential for the production of furfural, like oat hulls and corn cob residues, contain about 32% pentosan so that the practical achievable furfural yield can only be a maximum of about 10% of the dry substance of the raw material which is processed.

Since the raw materials have bulk densities or bulk specific gravities of about 250 kg/m³, with usual reactor fillings of about 50% and required residence times up to 5 hours, conventional processes require large reactor volumes.

Not only do large reactors take up large amounts of valuable space, but because of the fact that the reactors must be pressure type and corrosion resistant, they also involve high capital cost. Another problem with earlier methods from which furfural may be recovered is dealing with the residues which are contaminated with sulfuric acid.

OBJECTS OF THE INVENTION

It is, therefore, the principal object of the present invention to provide a process for the production of furfural in the highest possible concentrations with a minimum of capital and significantly reduced production costs.

Another object of the invention is to provide an improved method of making furfural whereby drawbacks of prior art approaches are avoided.

Yet another object of this invention is to provide an improved apparatus for carrying out this method or, stated otherwise, to provide an improved apparatus for the economic production of furfural.

SUMMARY OF THE INVENTION

These objects and others which will become apparent hereinafter are attained, in accordance with the invention, by a process for producing furfural which comprises:

(a) passing a suspension of a comminuted pentosan-containing raw material in dilute sulfuric acid continuously through a flow reactor and mixing the suspension in the reactor with high-pressure steam to heat the suspension to a temperature between 170° and 230° C. for a residence time sufficient to hydrolyze and dehydrate pentosan in the ray material to furfural, thereby forming a reacted suspension containing furfural which is discharged from the flow reactor;

(b) cooling the reacted suspension discharged from the reactor in a heat exchanger to a temperature between 140° and 200° C.;

(c) thereafter passing the reacted suspension, cooled ni the heat exchanger, through a valve into an expansion evaporator maintained at a pressure of at most 760 Torr to separate a residual suspension phase containing furfural from a water/furfural mixed vapor phase; and (d) recovering furfural from the vapor phase.

In apparatus terms, the invention can comprise:

means for forming a suspension of a comminuted pentosan-containing raw material in dilute sulfuric acid;

a flow reactor:

means for passing the suspension continuously through the flow reactor and mixing the suspension in the reactor with high-pressure steam to heat the suspension to a temperature between 170° and 230° C. for a residence time sufficient to hydrolyze and dehydrate pentosan in the raw material to furfural, thereby forming a reacted suspension containing furfural which is discharged from the flow reactor;

a heat exchanger connected to the flow reactor for cooling the reacted suspension discharged from the reactor to a temperature between 140° and 200° C.;

a valve connected to the heat exchanger for controlling and maintaining pressure;

an expansion evaporator connected to the valve and receiving the cooled reacted suspension from the heat exchanger therethrough and maintained at a pressure of at most 760 Torr to separate a residual suspension phase containing furfural from a water/furfural mixed vapor phase; and means connected to the expansion evaporator for recovering furfural from the vapor phase.

In particular, I have found that the transformation of pentosan in organic raw materials, including those mentioned above, to furfural, and the economic recovery of furfural, can be attained without the drawbacks previously mentioned if the previously comminuted raw material is suspended in dilute sulfuric acid, the suspension is continuously fed through a flow reactor, high pressure steam is fed to the flow reactor to heat the suspension to a temperature between 170° and 230° C., preferably 210° to 230° C. to form furfural in accordance with the reaction formula (3) referred to previously, and to separate the furfural from the remainder of the product, as an initial step, the reacted suspension is introduced into an expansion evaporator.

According to this invention, the reacted suspension is fed to the expansion evaporator through a valve which allows the pressure to be maintained and is expanded from a temperature between 140° and 200° C. to a pressure as maintained in the evaporator which is less than or equal to 760 Torr, but preferably is between 50 and 200 Torr.

To bring the reactive suspension to this lower temperature, it is a feature of the invention that the suspension discharged from the flow reactor is passed through a heat exchanger in which it is cooled to the aforementioned temperature of 140° to 200° C. and which is located upstream of the valve.

The rate of the overall reaction is improved with the use of dilute, for example 2% sulfuric acid under the conditions described.

The reaction or residence time in the flow reactor can be reduced to the order of seconds and at temperatures as low as 170° C. for the reaction, I note a significant advantage over conventional furfural processes.

It has been found that the optimum reaction temperature is between 210° and 230° C.. A temperature above 230° C. should not be utilized since, at such temperatures furfural is strongly polymerized in acid medium to reduce the yield and create problems with encrustation of the reactor walls.

The ratio of the required reaction space to the product rate is especially advantageous at the low residence time of the process of the invention.

For example, the reaction volume or space may be the same with the method of the invention as that of the process disclosed in U.S. Pat. No. 4,533,743, although there the production rate is significantly lower so that the process has a much lower yield and therefore a much lower furfural concentration in the output.

The process of the present invention has a number of other advantages by comparison with conventional processes apart from the very short reaction time.

For example, I have found that the yield is significantly higher than is customary in the furfural industry to date, because of the relationship between the flow reactor, cooler and expansion evaporator. The short period of contact between the furfural and the acid at elevated temperatures which can be achieved with the invention appears to greatly reduce polymerization, at least partly accounting for the increased yield.

Of special advantage by comparison with the conventional furfural processes is that the furfural-containing condensate is obtained, in accordance with the invention, in a form completely free from solids.

In conventional processes, for example, utilizing a fluidized bed, it is found that raw material particles are entrained by the vapor phase from the fluid bed and because of the long residence time in the reactor, tend to resinify therein, to form sticky adherent deposits.

Furthermore, in the cooling of the condensate resulting from the conventional processes, problematical wax-like deposits tend to form in addition to these particles, likewise apparently a consequence of the long residence times.

These various solids create significant problems in obstructing the reactor ducts, in collecting upon walls and in increasing the cost for separating them from the condensate.

Part of the high yield of the present invention can apparently be accounted for by the explosive-like or flash expansion of the solids particles in the expansion evaporator which is under a pressure preferably less than 760 Torr and more preferably between 50 and 200 Torr.

An azeotropic furfural/water system with a boiling point below that of water is liberated from the solids particles by this expansion and the consequent azeotropic evaporation. The expansion to a subatmospheric pressure ensures an increased furfural concentration in the expansion vapor phase. This effect is a consequence of the fact that the equilibrium line in the furfural/water system experiences a sharp shift to greater amounts of furfural in the vapor phase with decreasing pressure. A high furfural concentration is also promoted by the intervening cooling so that in the expansion evaporator, for example a cyclone, the vapor volume is reduced, thereby contributing to an increase of the furfural concentration in this vapor phase.

The enrichment of the expansion vapor with furfural directly results in an increase in the yield and can be enhanced when the reacted suspension prior thereto is cooled.

I have found it to be advantageous to have the suspension in the mixer at a temperature of about 95° C. and to feed this suspension by means of a volumetric or positive displacement pump, e.g. a screw pump, through the flow reactor and the cooler, while providing a valve, such as a pressure-limiting valve between the cooler and the expansion evaporator to maintain a constant higher pressure upstream of this valve.

The injection of high pressure steam into the flow reactor at the inlet end thereof increases the temperature of the reaction system to a point just below the boiling point and thus ensures the desired hydrolysis reaction reaction (conversion of pentosan to pentose) as well as the liberation of water from the pentose to transform the pentose to furfural.

After leaving the flow reactor, the suspension is cooled from its temperature level of 170° C. to 230° C., preferably 210° to 230° C. to a temperature of 140° to 200° C.

After traversing the pressure control valve, the reacted suspension enters the expansion evaporator which preferably is formed as a cyclone or like apparatus for separating the vapor phase which is thus formed from a solids-containing residual suspension.

The expansion evaporator is connected to a vacuum pump via at least one condenser and can be held at the recited subatmospheric pressure preferably between 50 to 200 Torr by a controller and a microvalve.

If the process is carried out with a temperature in the reactor of about 230° C. and the reacted suspension is expanded to atmospheric pressure (1 atmosphere) without intervening cooling, it is possible to obtain a ratio A of the furfural concentration in the condensate to the furfural concentration in the suspension fed to the expansion of 2.85 and a ratio B of the furfural mass flow in the condensate to the furfural mass flow in the suspension flowing into the expansion cyclone of 0.725.

These values represent significant improvements by themselves with respect to the conventional process.

With the intervening cooling, i.e. cooling of the reacted suspension in the heat exchanger before expansion while retaining the same ratio B=0.725, i.e. with equal expansion yield, I have found it to be possible to reach a ratio A of 4.22 when the reacted suspension at 230° C. is cooled to 150° C. and from this state is expanded into an expansion cyclone at a pressure of 0.25 atmospheres (190 Torr).

The furfural concentration n the concentrate is in this case greater by a factor F=4.22/2.85 of 1.48.

This advantage has the drawback that with a given temperature, water temperature of the cooling water supplied to the condenser, the condenser must be larger than in the case of expansion to atmospheric pressure. This disadvantage, however, is trivial by comparison with the greatly enhanced furfural concentration. According to a feature of the invention, in step (d), the water/furfural mixed vapor phase is subjected to condensation in a first condensing stage to yield a furfural-containing condensate and a vapor having a higher furfural content. This vapor, having the higher furfural content, is then condensed in a second condensing stage while the condensate of the first condenser is fed to the being preparation of the raw material to be fed to the reactor as part of the suspending liquid thereof.

The two-stage condensation has been found to increase the furfural concentration without wasting energy and water because of the recycling of the hot condensate from the first condenser to the preparation stage of the raw material, i.e. to the bagasse in a premixer. This advantage in water and heat recycle is accomplished without loss of furfural.

According to another feature of the invention, the residue suspension is displaced by a volumetric pump to a dewatering device.

The solids are recovered with a very low water content from this apparatus and the separated process-water which contains residual acid and residual furfural and is still hot, is recycled to a premixer to form a mash with the raw material. This also contributes to a saving of energy and fresh water and ensures that the acid will be largely recycled.

According to a further feature of the invention, the residual suspension phase is fed to a filter at which a solid is separated from a filtrate, the solid being initially subjected to extraction of moisture and then washed with water. Both the liquid recovered by the moisture extraction and a liquid formed by evaporative concentration of the wash water are then utilized to form a mash of fresh quantities of the raw material. Vapors from the evaporative concentration are then condensed for recovery of furfural therefrom.

In the latter mode of operation, the greater part of the acid contained in the residual suspension is recovered in the filter and is recycled to form a mash with the raw material. Residual acid is then washed with water from the solid phase on the filter so that the solid residue is practically acid-free. This allows further use of the solids which is not possible with at least some earlier processes.

The liquid phase which is initially recovered as the filtrate can be directly fed back to the raw material preparation stage.

The washing liquids can be subjected to concentration in the manner described so that the acid concentration in the residual liquid can be increased before it is recycled to the mash forming stage, for example, to a concentration of 2% acid.

Since the acid is recycled, the apparatus need only supply makeup quantities of the acid. The yield of furfural is increased, the cost of operating the process is decreased and environmental problems resulting from waste treatment are reduced or eliminated, especially since acid-laden solids need not be processed.

For a continued process, in accordance with the present invention, a maximum of 10% of the process water is branched off and separately distilled and is replaced by makeup acid while furfural and acid are recovered therefrom. That ensures that there will always be some extraction of nonvolatile contaminants, especially sugars and slowly-forming polymerization products of furfural which might otherwise tend to build up by the recycling.

With respect to the apparatus aspects of the invention, I note that it is advantages to displace the suspension of the precomminuted raw material and aqueous sulfuric acid, formed in an appropriate mixer, into the flow reactor through a volumetric pump which preferably is an eccentric worm or eccentric screw pump so that the residence time of the suspension in the flow reactor can be established and controlled to obtain the optimum relationship described previously.

The superatmospheric pressure in the flow reactor can be ensured by providing the flow reactor with a valve at its downstream end connected with the expansion evaporator.

The vapor mixture of furfural and water can be either subjected to further treatment by distillation in the conventional way either directly or after an intervening liquefaction in an appropriate condensation system.

Of course, in accordance with the invention in its best mode form, a heat exchanger is provided between the downstream end of the flow reactor and the expansion evaporator.

Advantageously, a drum-type filter is provided to receive the residual suspension and to dewater it and to then rinse or wash the solids which have been thus dewatered.

After separation of the washing liquid, a practically acid-free solid residue is obtained which can be dumped on a landfill or stored or worked-up further for use without difficulty.

All of the product-contacting parts of the apparatus which are to be at high temperature, preferably are composed of a nickel-copper malleable alloy, for example 28 to 34% by weight copper, 1.0 to 2.5% by weight manganese, 0 to 0.5% by weight silicon, 0 to 0.16% by weight carbon, 0 to 0.24% by weight sulfur and nickel plus cobalt in an amount of at least 63.0%. The alloy can be used as a cladding for those parts of the apparatus adapted to contact the reacting substances at elevated temperature.

BRIEF DESCRIPTION OF THE DRAWING

The above and other objects, features and advantages of the present invention will become more readily apparent from the following description, reference being made to the accompanying drawing in which.

SPECIFIC DESCRIPTION AND EXAMPLES

The Figures represent three examples of the process of the invention showing diagrammatically the apparatus used in each case and, of course, omitting the various control elements which customarily are used and required.

Figure 1:
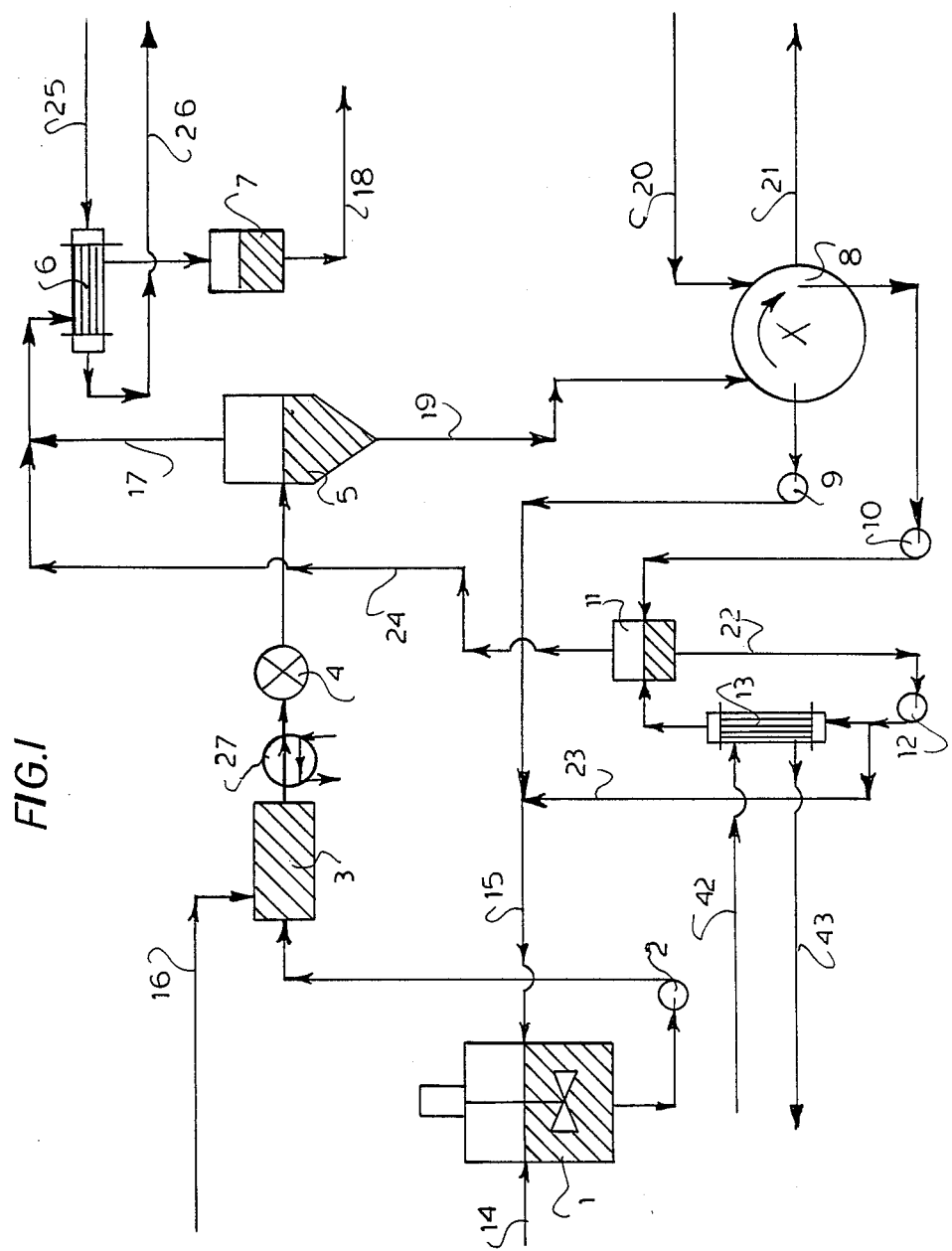
FIG. 1 is a flow diagram illustrating the method of the invention illustrating the treatment of the residual suspension from the expansion evaporator.

In the method of FIG. 1, precomminuted raw material, for example, wood scrap such as sawdust and the like, dewatered by pressing, is fed via line 14 to a mixer 1 and is there mixed with about 2% aqueous sulfuric acid as delivered by the line 15.

By means of a volumetric pump, for example, an eccentric worm pump represented diagrammatically at 2, the thus-produced suspension is drawn from the mixer and fed to a flow reactor 3 which can be a tube-loop reactor held at a constant pressure by a valve 4 provided at the downstream end of this reactor. A cooler 27, as described in greater detail below, is interposed between the downstream end of the reactor 3 and the valve 4.

Via a line 16, high pressure superheated steam is introduced into the flow reactor 3 at its upstream end to raise the temperature of the contents of the reactor to the reaction temperature of about 230° C. to accelerate the actions represented by equations 1 and 2.

The flow reactor 3 is so dimensioned that, at the selected temperature, the volumetric pump 2 can displace the suspension through the reactor at the rate at which conversion of pentosan to furfural occurs.

After traversing the valve 4, the suspension expands to atmospheric pressure in the expansion evaporator 5.

The resulting vapor phase containing water and furfural is fed at 17 to a condenser 6. The condensate (a mixture of furfural and water) is collected in the vessel 7 and can be fed via line 18 to the usual distillation process for recovery of the furfural.

With an expansion from 230° C. to 100° C. and typical furfural concentration, about 70% of the furfural delivered to the expansion evaporator 5 is found in the vapor phase. The remainder passes with the residual suspension via line 19 onto a drum-like filter where the greater portion of the liquid component is separated and is returned by the pump 9 to the mixer 1.

The solids, thus freed from most of the liquid phase, are then washed on the drum filter by wash-water supplied via line 20 and the solids residue is discharged at 21, for example, via a squeezing or pressing roller, now shown.

The pump 10 displaces acid-containing and furfural-containing washing water to a vapor separator 11. From the latter, a line 22 and a pump 12 displace the liquid phase to a heat exchanger 13 which serves to heat the liquid to the boiling point before it is returned to the separator 11. The acid is thereby concentrated in the liquid phase so that via line 23 this liquid can be combined with the liquid initially extracted by the drum 8 and can be supplied at an acid concentration of about 2% to the mixer 1.

The furfural-enriched vapors from the separator 11 are delivered by line 24 to the condenser 6, thereby joining the vapor from line 17. As a consequence, no furfural is lost with the solids. The cooling water feed and return lines for the condenser 6 are represented at 25 and 26 while a steam-feed line 42 and a condensate-return line 43 communicate with the heater 13 in which steam is used as the heating medium.

Figure 2:
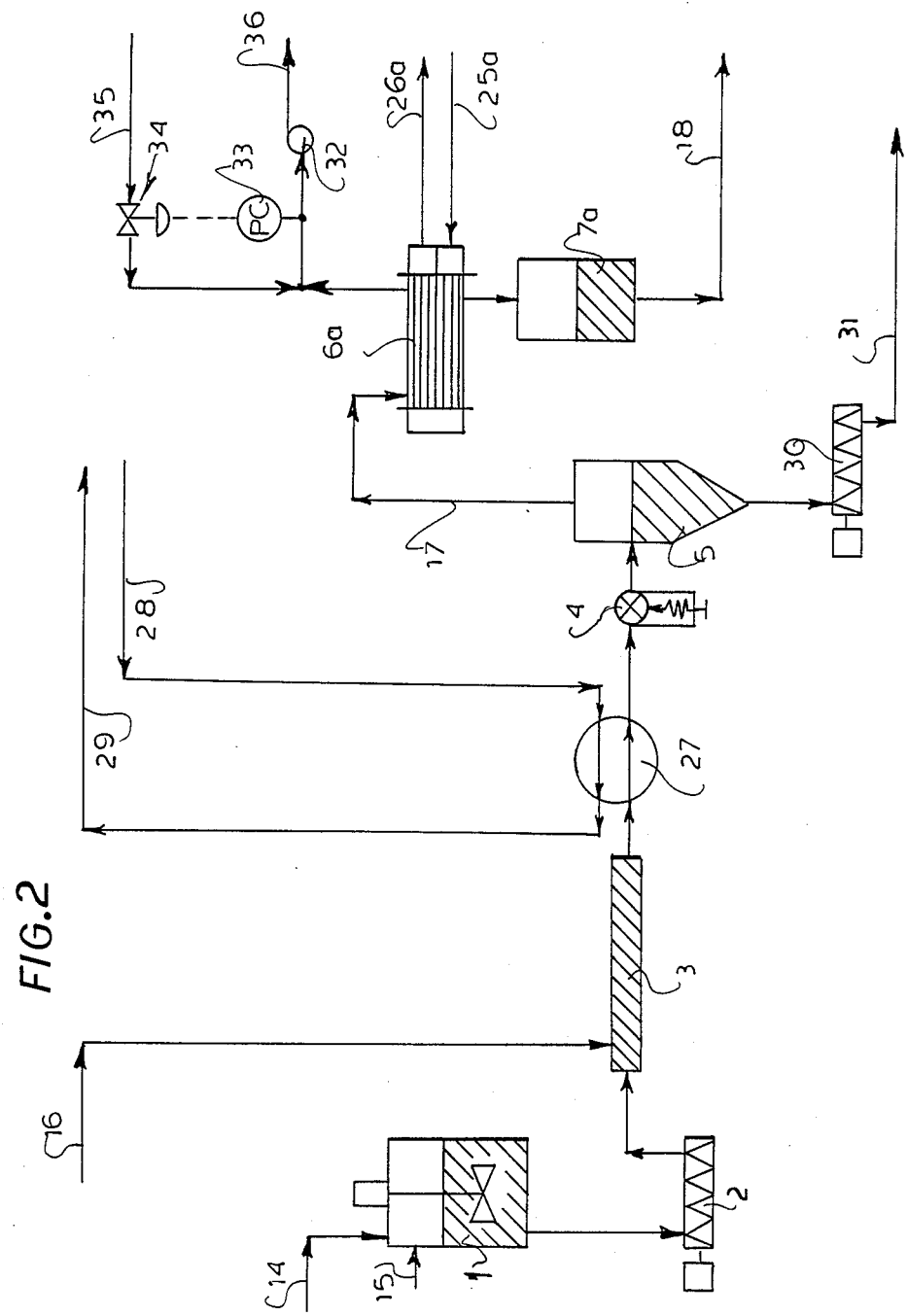
FIG. 2 is a flow diagram illustrating the process of the invention with an expansion evaporator operated at reduced pressure.

In the method represented by the flow diagram of FIG. 2, a pentosan-containing precomminuted raw material is delivered at 14 to the mixer 1. The raw material in this case can be bagasse.

The raw material is mixed with water-diluted sulfuric acid supplied at 15 in the mixer 1 to a flowable pulp suspension. The commutation can be effected by a rotor-stator machine similar to that described in European patent document No. 0 253 139.

Via the volumetric pump 2, for example, an eccentric worm pump, this suspension is delivered to the tube coils of the flow reactor 3 in the region of the inlet end of which high-pressure steam is injected at 16.

The reacted suspension from the flow reactor 3 is passed through a cooler 27 having a cold-water feedline 28 and a cooling-water discharge line 29, upstream of the valve 4.

The suspension is forced, after cooling, past the pressure control valve 4 into the expansion evaporator 5 which is formed as a cyclone.

The valve 4 serves to set and maintain the pressure within the reactor 3.

The suspension residue which is separated in the cyclone 5 can be drawn off by a pump 30, e.g. an eccentric worm pump, and fed via line 31 to an after-treatment stage which can be similar to the treatment stage represented in FIG. 1.

The expansion vapors and mist are supplied by the line 17 to a condenser 6a in which they are liquefied. The cold-water supply line for this condenser 6a is shown at 25a while the water return line is seen at 26a.

Condensate collects in a vessel 7a and is drawn off via line 18.

The subatmospheric pressure in the expansion devices 5 and condenser 6a is maintained by a vacuum pump 32 and by a pressure controller 33 operating a valve 34 for setting the vacuum and controlling the admission of air from a vent line 35. The air discharge is represented at 36.

Figure 3:
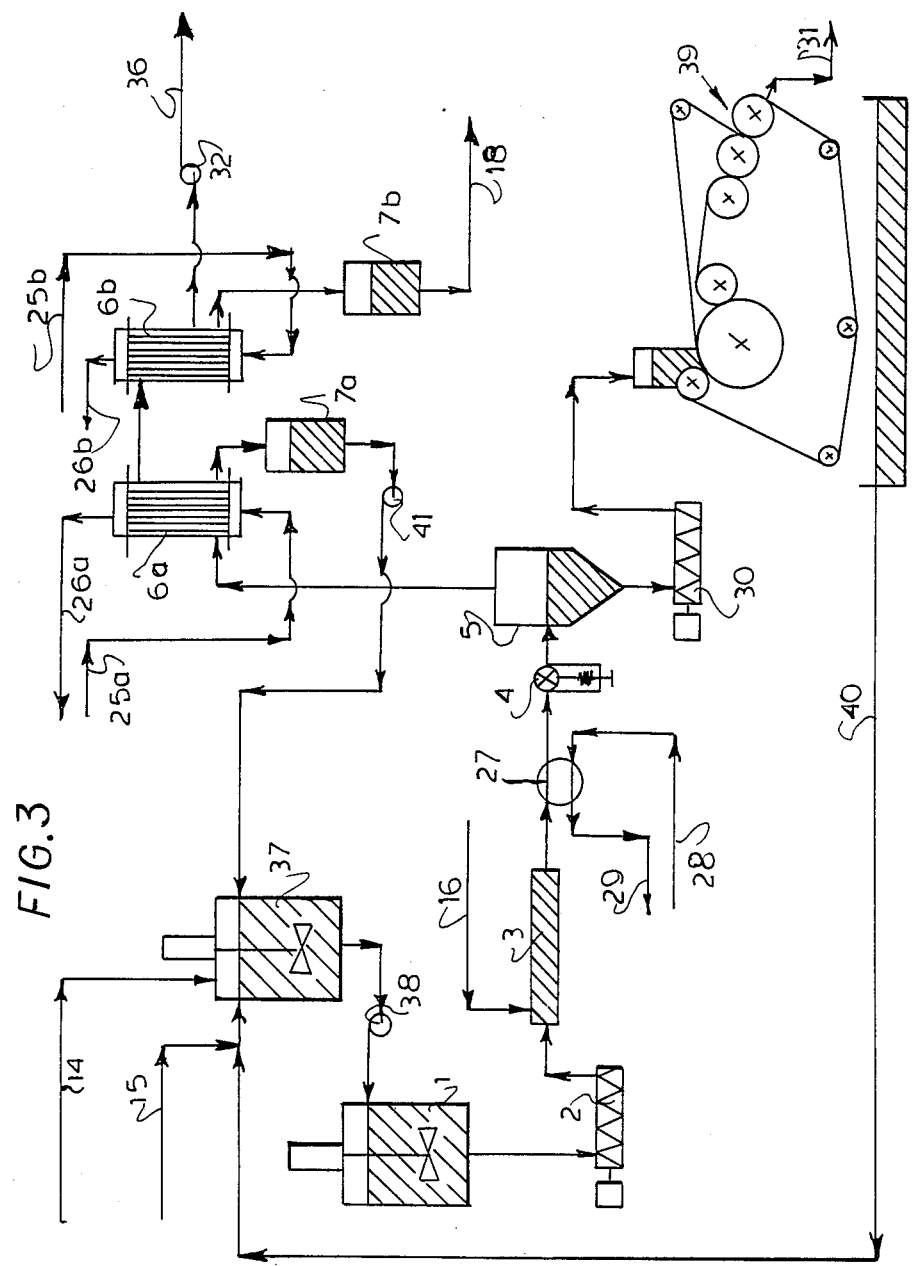
FIG. 3 is a flow diagram of a process carried out with two-stage condensation and dewatering of the residual suspension.

In the process represented in FIG. 3, the suspension of pentosan-containing raw materials, e.g. bagasse, and 2% sulfuric acid is fed from the mixer 1 by the volumetric pump 2 to the reactor 3.

This reactor again is a tube coil or tube-loop reactor which is provided at its inlet end with high-pressure steam introduced by line 16.

The steam heats the suspension to, for example, 230° C.. The reacted suspension leaving the reactor 3 is cooled in the heat exchanger 27 which has cooler-water inlet and outlet lines 28 and 29, to a temperature of, for example, 160° C.. The suspension then passes the pressure control valve 4 which controls and maintains the pressure in the flow reactor 3 in accordance with the predetermined temperature.

After passing the valve 4, the suspension is expanded in the expansion evaporator 5, preferably a cyclone, to about 190 Torr. This corresponds to a temperature of 65° C..

Because of the explosive-like expansion and evaporation, the greatest part of the furfural is liberated by azeotropic cavitation and is carried away in the vapor phase.

The residual suspension is fed by the volumetric pump 30 to a dewatering unit 39 in which most of the water contained in the suspension is recovered together with the sulfuric acid dissolved therein. The dewatered solids, with a dry substance content of, for example, 40% is discharged at 31.

The furfural-containing vapor from the expansion evaporator 5 is fed to a first condenser 6a which effects an increase of the furfural concentration in the vapor phase. The liquid phase, relatively low in furfural, is collected from the condenser 6a in a vessel 7a and fed via a pump 41 to a premixer 37.

The remaining vapor phase from the condenser 6a, containing the bulk of the furfural, is fed to the condenser 6b for liquefaction therein.

A vacuum pump 32 is connected to the condenser and has its air outlet indicated at 36. The condensers 6a and 6b have respective water inlets and outlets 25a, 26a and 25b, 26b.

In the premixer 37, the comminuted raw material is mixed with the process water recovered at the dewatering apparatus 39, the condensate from the first condenser 6a and, to make up for losses, the requisite quantity of dilute sulfuric acid.

The result is a suspension with relatively coarse solids. This suspension is comminuted in or processed through a rotor-stator machine of the type described in the aforementioned Europatent publication to a suspension with very fine, uniformly distributed raw material particles, this fine suspension bed fed to the mixer 1.

I claim:

1. A process for making furfural, comprising the steps of:
    (a) passing a suspension of a comminuted pentosan-containing raw material in dilute sulfuric acid continuously through a flow reactor and mixing said suspension in said reactor with high-pressure steam to heat said suspension to a temperature between 170° and 230° C. for a residence time sufficient to hydrolyze and dehydrate pentosan in said raw material to furfural, thereby forming a reacted suspension containing furfural which is discharged from said flow reactor;
    (b) cooling the reacted suspension discharged from said reactor in a heat exchanger to a temperature between 140° and 200° C.;
    (c) thereafter passing the reacted suspension, cooled in said heat exchanger, through a valve into an expansion evaporator maintained at a pressure of at most 760 Torr to separate a residual suspension phase containing furfural from a water/furfural mixed vapor phase; and
    (d) recovering furfural from the vapor phase by distillation, either directly or after liquefaction.

2. The process defined in claim 1 wherein:
   the temperature to which the suspension is heated in said flow reactor is 210° to 230° C.; and
   said pressure is between 50 and 200 Torr.

3. The process defined in claim 1 wherein, in step (d) said water/furfural mixed vapor phase is subjected to condensation in a first condensing stage to yield a furfural-containing condensate and a vapor having a higher furfural content, and said vapor having said higher furfural content is then condensed in a second condensing stage, said condensate being fed to said reactor in step (a).

4. The process defined in claim 1 wherein said residual suspension phase is dewatered to form an acid and furfural containing process water, said process water being fed to said reactor in step (a).

5. The process defined in claim 1 wherein said residual suspension phase is fed to a filter at which a solid is separated from a filtrate, said solid being initially subjected to extraction of moisture and then washed with water, a liquid recovered by the moisture extraction and a liquid formed by evaporative concentration of the wash water being then utilized to form a mash of fresh quantities of said raw material, vapors of the evaporative concentration being then processed for recovery of furfural therefrom.

6. The process defined in claim 5 wherein said vapors of the evaporative concentration are combined with said water/furfural mixed vapor phase for recovery of furfural therefrom.

7. The process defined in claim 4 wherein a part of said process water is subjected to distillation prior to being fed to the reactor in step (a).

8. The process defined in claim 7 wherein said part is a maximum of 10% of said process water.

* * * * *